United States Patent [19]

Cunningham

[11] 4,436,097
[45] Mar. 13, 1984

[54] CARDIOVASCULAR EXERCISE APPARATUS

[76] Inventor: Patrick J. Cunningham, 350 Orangethorpe Ave., #27, Placentia, Calif. 92670

[21] Appl. No.: 385,464

[22] Filed: Jun. 7, 1982

[51] Int. Cl.³ .............................................. A61B 5/02
[52] U.S. Cl. .................................................. 128/707
[58] Field of Search .................. 128/706, 707; 272/69, 272/73, 93, 99, 100, 109, 116, 117, 125, 129-132, DIG. 5-6; 73/379

[56] References Cited

U.S. PATENT DOCUMENTS

| | | | |
|---|---|---|---|
| 3,395,698 | 8/1968 | Morehouse | 128/707 |
| 3,494,616 | 2/1970 | Parsons | 272/130 |
| 3,518,985 | 7/1970 | Quinton | 272/DIG. 6 |
| 3,572,699 | 3/1971 | Nies | 272/129 |
| 3,608,545 | 9/1971 | Novack et al. | 128/705 |
| 3,744,480 | 7/1973 | Gause et al. | 128/707 |
| 3,802,698 | 4/1974 | Burian et al. | 272/73 |
| 3,845,756 | 11/1974 | Olsson | 73/379 |
| 3,964,742 | 6/1976 | Carnielli | 272/73 |
| 4,378,111 | 3/1983 | Tsuchida et al. | 73/379 |

FOREIGN PATENT DOCUMENTS 2449440  4/1975  Fed. Rep. of Germany ........ 272/73

OTHER PUBLICATIONS

Jacobsen et al., "An Ergometer Bicycle Controlled By Heart Rate", *Medical & Biological Engineering*, Sep. 1974, pp. 675-680.
Fitron Cycle Ergometer Brochure Lumex Inc. 5/82.
Tunturi Brochure–Tunturipyörä Oy, 10/79.
Dynavit Brochure–Dynavit of America.
BH Brochure–Union 76, Merchandising Ctr.

Primary Examiner—William E. Kamm
Assistant Examiner—Mitchell J. Shein
Attorney, Agent, or Firm—Hubbard & Stetina

[57] ABSTRACT

A cardiovascular exercise apparatus is disclosed comprising a support frame adapted to carry a user thereon including a pair of separate means for providing aerobic exercising of both the upper and lower body portions of the user. Both of the exercising means are governed by a hydraulic motor/regulator which applies a preset, variable exercise load or torque to the exercising means. Biofeedback means are additionally provided to monitor the heart rate of the user during the exercise and control the hydraulic regulator to reduce and/or terminate the exercise load in response to the user's heart rate exceeding a preset limit for the particular exercise time period.

14 Claims, 4 Drawing Figures

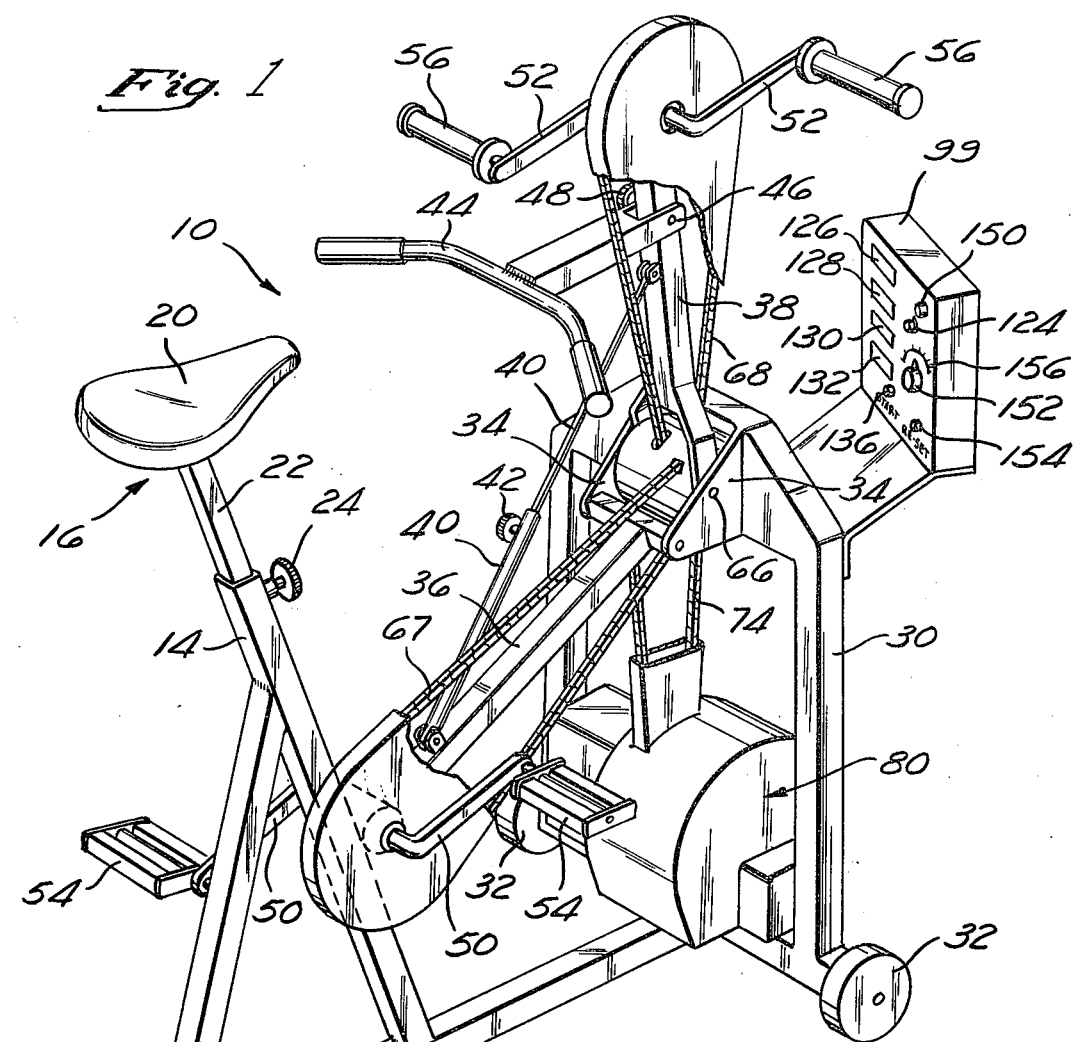
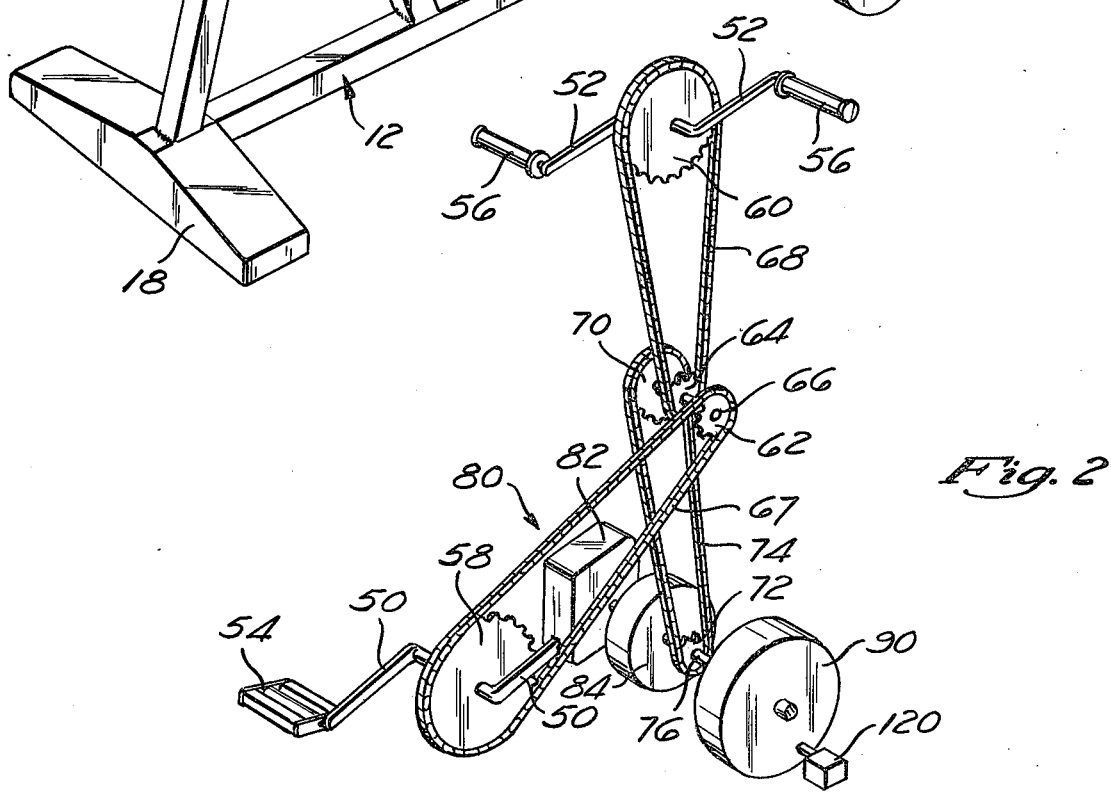

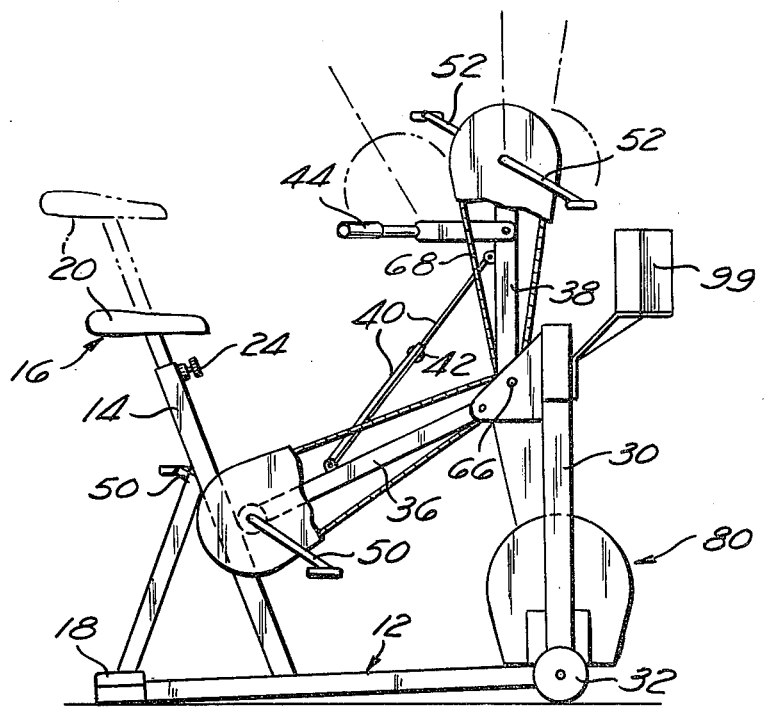
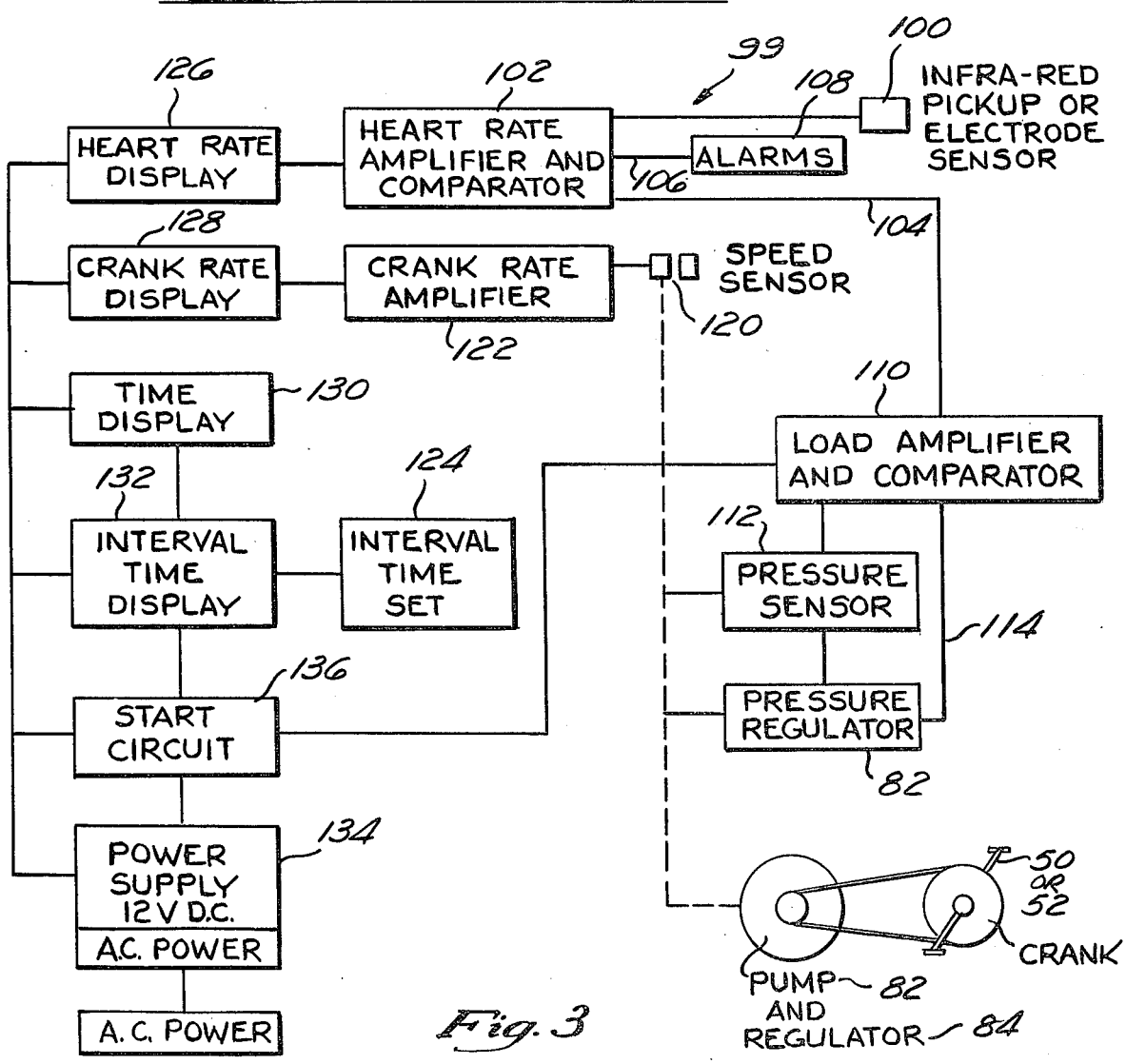
Fig. 4
Fig. 3

CARDIOVASCULAR EXERCISE APPARATUS

BACKGROUND OF THE PRESENT INVENTION

The present invention relates to exercise apparatus and more particularly to a cardiovascular exercise apparatus which includes means for providing aerobic exercising of both the upper and lower body portions of the user and including biofeedback means for monitoring the heart rate of the user and reducing or terminating the exercise load in reponse to the user's heart rate exceeding a preset limit.

In recent years, the medical profession has recognized the importance of exercise in cardiovascular health with most physicians now prescribing moderately intense aerobic exercise programs for heart rehabilitation and preventive care. In this regard, physicians are routinely recommending cycling as a preferred form of aerobic exercise effective in cardiovascular conditioning.

In response to this professional recognition, a variety of exercise and stress analysis equipment have been introduced in the marketplace. Basically, the majority of the prior art cardiovascular exercise equipment can be segregated into two classifications: (1) treadmills and ergometers adapted primarily for clinical testing and rehabilitation applications and (2) cycling exercise apparatus predominantly utilized for residential use.

The prior art professional treadmills and ergometers have typically been extremely expensive due primarily to their inclusion of complex biofeedback means which provide a constant monitoring of many of the user's physical perameters (such as heart rate and blood pressure). In addition, due to such ergometers and treadmills being capable of overstressing cardiovascular activity during use, such apparatus have typically been utilized only in clinical applications where trained medical personnel can monitor the physical perameters of the user and modify the exercise program as required.

In contrast to the prior art professional apparatus, the majority of the prior art residential bicycle exercise apparatus have typically failed to provide the necessary biofeedback to monitor the user's cardiovascular performance during the exercise program. In addition, many of the prior art residential exercise apparatus have been poorly constructed and have often been incapable of providing sufficient load regulating tolerances during repetitive operations. Further, due to their failure to include any biofeedback monitoring, they have posed an inherent safety hazard in causing overstress conditions without giving any warning to the individual user.

Further, both the professional and residential prior art exercise apparatus have typically only been designed to exercise the lower portion of the body and have failed to address the need for upper body exercise which additionally has been found effective in improving cardiovascular health.

As such, there exists a substantial need in the art for an improved cardiovascular exercise apparatus which is relatively low cost to permit widespread residential as well as clinical use, provides aerobic exercise for both the lower and upper portions of the body, includes a biofeedback mechanism to permit monitoring of the cardiovascular system, and further, includes a safety mechanism which insures that cardiovascular overstressing is controlled or eliminated.

SUMMARY OF THE PRESENT INVENTION

The present invention specifically addresses this need and alleviates the above-referenced deficiencies associated in the prior art. More particularly, the present invention comprises a relatively low cost cardiovascular exercise apparatus which includes separate exercising means for providing aerobic exercise for both the upper and lower portions of the body. In addition, the exercise apparatus of the present invention includes a hydraulic pump/regulator mechanism which applies a preset variable exercise load or torque to the exercising means during the exercise operation program. Due to the pump/regulator being hydraulically operated, close tolerances on the applied exercise load or physical exertion required during the exercise program can be maintained and rapidly reproduced for repetitive exercise programs. As such, the present invention comprises a relatively sophisticated exercise apparatus which can be effectively utilized in both clincial and residential applications.

To augment these improved exercise program capabilities, the present invention additionally incorporates a novel biofeedback mechanism which continuously monitors the cardiovascular performance (i.e., heart rate) of the individual during the exercise program. In the preferred embodiment, the biofeedback mechanism permits a desired preset heart rate to be selected and programmed into the apparatus and when the heart rate of the individual exceeds this preset value, an audio warning is automatically generated to alert the individual of a possible overstress condition. As such, the present invention provides a significant improvement over the prior art residential exercise apparatus by alerting the user to the possible health hazard of continuing the exercise program.

In addition, the biofeedback mechanism of the present invention is coupled to the hydraulic regulator to reduce and/or terminate the exercise load in response to the user's heart rate exceeding the preset limit for a particular exercise time period. In the preferred embodiment, upon encountering an overstress condition, the biofeedback mechanism automatically reduces the exercise load to twenty percent of its initial value and maintains this reduced load for a 20 second interval. If during this 20 second interval the user's heart rate falls to a value below the preset heart rate limit, the exercise program continues with the load rating automatically resetting to its initial value. However, if the user's heart rate fails to decline below the preset limit within the 20 second period, the biofeedback means automatically actuates the load regulator to discontinue the exercise load and provide a free wheeling no load condition and generate an audio alarm. Thus, the present invention provides a passive safety mechanism which prevents continued cardiovascular overstressing during the exercising program.

In addition, the present invention provides a display of the heart rate, crank rate, program time and elapsed exercise time during operation which additionally may be altered by the user, and permits rapid adjustment of the seat and handlebar assembly to accommodate the differing physical size of individual users.

DESCRIPTION OF THE DRAWINGS

These as well as other features of the present invention will become more apparent upon references to the drawings, wherein:

FIG. 1 is a perspective view of the improved cardiovascular exercise apparatus of the present invention;

FIG. 2 is a perspective view of the chain linkage and drive mechanism of the cardiovascular exercise apparatus;

FIG. 3 is an electrical schematic diagram depicting the control circuit between the biofeedback mechanism and the hydraulic load regulator of the present invention; and FIG. 4 is an elevational view of the improved cardiovascular exercise apparatus illustrating the manner in which the same may be adjusted for the particular exercise program and size of individual users.

DETAILED DESCRIPTION OF THE PREFERRED EMBODIMENT

Referring to FIG. 1, there is shown the improved cardiovascular exercise apparatus 10 of the present invention. The exercise apparatus 10 includes a support frame 12 preferably formed of a plurality of tubular metal frame segments interconnected as by of weldments to form a rigid platform structure. The rear portion of the frame 12 includes a generally vertically extending A-frame section 14 which mounts a seat assembly 16 adapted to support a user (not shown) upon the apparatus 10 and a laterally extending foot plate 18 adapted to provide lateral stability for the frame 10 upon a support surface.

The seat assembly 16 is composed of a seat member 20 and mounting extension 22. The cross sectional dimensions of the mounting section 22 is sized to be slidingly received or inserted within the interior of the A-frame section 14. A hold-down knob 24 threadingly attached to the upper portion of the A-frame section 14 is provided to selectively secure the seat extension 22 and seat 20 in a desired vertical orientation relative the A-frame member 14.

The front portion of the frame 12 includes a yoke 30 which extends in a generally vertical orientation as well as a pair of wheels 32 formed to permit a selective transport of the entire apparatus 10 upon a support surface. A pair of mounting flanges 34 are attached at one end to the upper portion of the yoke 30 and at their opposite end to a cross bar member 36 extending to the A-frame section 14. The flanges 34 pivotally mount a generally Y-shaped support arm 38 which may be maintained in a desired pivotal orientation by adjustment of a pair of telescoping linkages 40 and a threaded lock knob 42 assembly extending angularly between cross bar member 36 and support arm 38. A handlebar assembly 44 is mounted proximal the median of the support arm 38 and is pivotally attached thereto as by way of a pivot shaft 46 and lock knob 48.

A pair of foot cranks 50 and hand cranks 52 are provided and are journaled in a conventional bearing assembly to one end of the cross bar 36 and support arm 38 respectively. A pair of foot pedals 54 and hand grips 56 are rotably attached to the distal ends of the foot cranks and hand cranks 52 which are adapted to support the feet and hand (not shown) respectively of a user in a conventional manner. Referring more particularly to FIG. 2, the foot cranks 50 are connected to a drive sprocket or gear 58 while the hand cranks 52 are similarly attached to a drive sprocket 60. Both of the drive sprockets 58 and 60 communicate with the respective driven sprocket 62 and 64 as by way of a pair of chain linkages 67 and 68. The driven sprockets 62 and 64 are mounted upon a common shaft 66 which extends laterally between the pair of mounting flanges 34 (as shown in FIG. 1) and are each mounted to the shaft 66 by a respective unidirectional coupling adapted to transmit rotational movement of the driven gears 62 and 64 to the shaft 66 in only a single direction while allowing the driven sprockets 62 and 64 to freely spin about the shaft 66 when rotating in a reverse direction. In the preferred embodiment, the unidirectional couplings are mounted on the respective driven gears 62 and 64 in opposition to one another such that when one of the driven gears 62 transmits rotational movement to the shaft 64, the other driven gear 64 is maintained in a free wheeling mode and conversely, when rotational movement is imparted to the shaft 66 by the driven gear 64, the other driven gear 62 is in a free wheeling mode.

A common sprocket 70 is rigidly mounted to one end of the common shaft 66 and as such, rotates whenever rotational movement is applied to the common shaft 66. The common sprocket 70 drives a control sprocket 72 as by way of a chain linkage 74 and is rigidly attached to a main drive shaft 76 journaled for rotational movement between the opposite sides of the yoke 30 of the frame 12. By such a structure, it will be recognized that rotation of either the foot cranks 50 or hand cranks 52, causes corresponding rotational movement of the common drive shaft 76.

To vary the torque or exercise load required to turn the shaft 76, the present invention utilizes a load regulating means designated generally by the numeral 80, which serves to provide a counteracting rotation force upon the shaft 76 in opposition to the rotation force applied by the foot cranks 50 and/or hand cranks 52. In the preferred embodiment, the load regulating means 80 comprises a hydraulic pump 84 and a pressure regulator 82 which is positioned on the pump 84 to vary the pressure and thus, vary the output torque of the pump 84 applied to the common shaft 76. To help eliminate minor speed variations in the rotational speed of the common shaft 76, a relatively large mass flywheel 90 is connected to the distal end of the common shaft 76.

By such a structure, it will be recognized that by varying the pressure applied to the hydraulic pump 84 from the regulator 82, a user may adjust the torque (i.e., the amount of dynamic braking or exercise load) applied to the common shaft 76 which acts in opposition to the rotation force being applied to the common shaft 76 by rotation of the foot cranks 50 and/or hand crank 52. It will additionally be recognized that due to this counterrotational torque being applied by the hydraulic pump 84 rather than by a conventional brake or the like, the magnitude of the opposing force or load being applied to the common shaft may be accurately adjusted between minimum and maximum value and be accurately reproduced during repeated exercise programs.

To augment the improved structural design discussed above, the present invention additionally incorporates a novel biofeedback system which permits the monitoring of the heart rate of the user during the exercise program and automatically modifies the exercise program of the apparatus 10 in response to the detection of changes in the heart rate of the user. The particular electrical circuitry 99 of the novel biofeedback system of the present invention is illustrated in FIG. 3.

Basically, the biofeedback system comprises an infrared pick up or electrode sensor 100 which may be attached in a conventional manner to a user during the exercise program to detect the heart rate of the user and generate an electrical signal which in the preferred embodiment, is applied to a heart rate amplifier and comparator 102. Such heart rate amplifiers and comparators are well known in the electronics art and permit a preset value to be stored within the amplifier and comparator 102 and be constantly compared with the signal values obtained from the sensor 100. In the particular circuitry 99 of the present invention, if the signal value obtained from the sensor 100 is less than the preset value stored within the comparator, a first output signal is applied to the main output branch 104 of the amplifier and comparator 102; while if the signal obtained from the sensor 100 is above the preset value stored in the amplifier comparator 102, an auxiliary output signal is applied to a second output branch 106 of the amplifier and comparator 102. As shown in FIG. 3, the second branch 106 of the amplifier and comparator 102 is connected to a suitable alarm 108 which in the preferred embodiment comprises an audible alarm adapted to generate a tone to warn the user of his actual heart rate being greater than the preset value stored in the amplifier and comparator 102.

The main output branch 104 of the heart rate amplifier and comparator 102 controls a load amplifier and comparator 110 which is constructed and functions in a similar manner to the heart rate amplifier and comparator 102. The load amplifier and comparator 110 is connected to receive an input signal from a pressure sensor 112 adapted to monitor the pressure applied to the pump 84 and motor 84 through the pressure regulator 82. As with the heart rate amplifier and comparator, the load amplifier and comparator allows a preset load value to be stored therein and continuously compares the signal value obtained from the pressure sensor 112 with the preset stored value. When the signal value obtained from the pressure sensor 112 is greater than the stored value within the load amplifier and comparator 110, a signal is applied to the output 114 of the load amplifier and comparator to throttle down the pressure regulator 82 and reduce the pressure applied to the pump 84 and, hence, reduce the torque load applied to the cranks 50 or 52. Conversely, when the signal received from the pressure sensor 112 is less than the stored value within the load amplifier and comparator 110, the electrical signal is applied to the output 114 of the load amplifier and comparator 110 serves to open the pressure regulator 82 and increase the pressure and hence, increase the torque load applied to the crank 50 or 52.

The circuit 99 additionally includes a speed sensor 120 which is preferably mounted relative the flywheel 90 (as shown in FIG. 2) to produce a signal which is applied to a crank rate amplifier 122. A timer 124 including an interval time set is additionally provided and is connected in the circuit 99 to provide the time interval for the exercise program. In the preferred embodiment, the heart rate amplifier and comparator 102, crank rate amplifier 122, and timer 124 are connected to respective conventional displays 126 through 130 to permit visual observation of the heart rate, crank rate, and elapsed time while the timer 124 additionally includes an exercise internal time display 132 which displays the total predetermined interval time set for the exercise program. A conventional AC/DC power converter 134 is additionally provided which includes an on/off switch 154 (shown in FIG. 1) to apply power to the circuit while an exercise start circuit 136 is additionally provided to initiate the operation of the timer 134.

With the structure defined, the operation of the exercise apparatus 10 and biofeedback system of the present invention in an exercise program may be described. Referring jointly to FIGS. 3 and 4, a user may initially adjust the heighth of the seat assembly 16 relative the frame 12 between the full line and phantom line positions indicated in FIG. 4, and lock the same into position by tightening the hand knob 24. In those instances when the user desires to exercise the lower portion of his body, the user can pivot the arm member 38 and pair of hand cranks 52 to a maximum clockwise position indicated by phantom lines in FIG. 4 so as to be stowed in a noninterferring position. Subsequently, the user may adjust the pivotal orientation of the handlebars 44 by loosening and tightening the hand knob 48 cooperating with the handlebars 44 as shown in FIG. 1. Alternatively, in those instances when the user desires to utilize the the hand cranks 52, as opposed to the foot cranks 50, the support arm 38 may be pivoted and subsequently locked in a desired counterclockwise pivotal orientation as indicated in the phantom lines in FIG. 4 with the handlebars additionally being pivoted to their fully counterclockwise orientation so as to be disposed in an orientation which would not interfere with the manual turning of the hand cranks 52.

With the apparatus 10 adjusted in such a manner, the user may turn the power switch 154 (shown in FIG. 1) to an "on" position connecting the 12 volt DC power supply 134 to the electrical circuit 99. The heart rate adjustment knob 150 may then be manually turned to enter a desired heart rate value for storage in the heart rate amplifier and comparator 102. As will be recognized, during the adjustment of the heart rate knob 150, the desired entered value is displayed on the heart rate display 126. The time duration of the exercise program may additionally be set by manually turning the time interval adjustment knob 124 which generates a visual display of the time interval on the interval time display 132. The load adjust knob 152 may be similarly turned to a desired position indicated by a percent load scale 156 which is effective in storing the predetermined load value in the load amplifier and comparator 110.

With the above operative steps completed, the user may begin peddling the foot cranks 50 or hand cranks 52 in a conventional manner, wherein due to the rotation of the flywheel 90, the speed sensor 120 generates a signal which is applied to the crank rate amplifier 122 and continuously displayed on crank rate display 128. When it is desired to initiate the exercise program, the user simply presses the start circuit switch 136 which causes the elapsed time to be displayed on the time display 130. As the exercise program continues, the heart rate signal generated from the pick up or sensor 100 is constantly displayed on the heart rate display 126 and is compared with the stored preset value by the heart rate amplifier and comparator 102. Assuming that the sensed heart rate signal is less than stored value, the primary output signal of the heart rate amplifier and comparator 102 causes the load amplifier and comparator 110 to function in its primary operational mode. In this primiary mode, the load comparator 110 monitors the load applied to the pump 84 and motor 84 by comparing the signals received from the pressure sensor 112 with the predetermined value previous stored in the load amplifier and throttles the pressure regulator 82 to maintain a constant torque applied to the cranks 50 or 52.

When and if the sensed heart rate signal applied to the heart rate amplifier and comparator 102 exceeds the preset stored value, an auxiliary output signal is applied to the secondary output of the heart rate amplifier and comparator 102 to energize the audible alarm 108 and warn the user of an overstress condition. Simultaneously, the primary output signal from the heart rate amplifier and comparator 102 is modified to send a signal to the load amplifier and comparator 110 to initiate a secondary operational mode which is effective in causing the pressure regulator to be throttled down to reduce the load applied to the foot or hand crank 50 and 52 to approximately 20 percent of its initial value.

In the preferred embodiment, the secondary signal applied to the alarm 108 and secondary operational mode of the load amplifier and comparator 110 is maintained for a 20 second period at which time if the heart rate signal generated from the sensor 100 has decreased below the preset stored value, the primary signal from the heart rate amplifier and comparator 102 is again modified back to its initial value and the load amplifier and comparator 110 resets back to its primary operation mode to open the pressure regulator 82 to increase the pressure and thus the load applied to the hand or foot cranks 50 and 52 back to its initial value.

Alternatively, if the heart rate signal obtained from the sensor 100 fails to fall below the preset stored value within the 20 second time interval, the primary signal from the amplifier and comparator is discontinued which causes the load amplifier and comparator 110 to deactivate the regulator 82 and allow the foot or hand cranks 50 and 52 to go into a free wheeling mode wherein no counterrotational force is applied to the cranks 50 or 52. Hence, it will be recognized that the present invention yields a passive safety feature which prevents any cardiovascular overstressing of a user during the exercise program.

Assuming that the heart rate signal applied to the heart rate amplifier and comparator 102 returns below the preset stored value or alternatively, that the preset value was never exceeded, the exercise program continues until the elapsed time equals the time previously set on the interval time display 132 wherein the signal applied to the load amplifier and comparator 110 discontinues to control the regulator 82, removing the load applied to the crank 50 and 52 and signal the end of the exercise program.

Those skilled in the art will recognize that by use of the apparatus 10 of the present invention, the load, time interval, and heart rate may be rapidly modified during the actual exercise program to insure that the proper amount of cardiovascular stress exercise is yielded. In addition, those skilled in the art will recognized that although in the preferred embodiment, particular time intervals and load reductions have been illustrated, variations to the same may be readily made without departing from the spirit of the present invention and such modifications are clearly contemplated herein.

What is claimed is:

1. An improved cardiovascular exercise apparatus comprising:
   a frame adapted to support a user thereon;
   means carried by said frame and adapted for manual rotatable movement in a first direction for providing aerobic exercising of the upper body of said user;
   means carried by said frame and adapted for manual rotatable movement in a first direction for providing aerobic exercising of the lower body of said user; and
   means for applying a pre-determined force in opposition to and independent of the rotatable movement of said upper and lower aerobic exercising means, wherein said opposition force applying means comprises a hydraulic pump connected to rotate a common rotable shaft cooperating with said upper and lower aerobic exercising means in a secon direction, opposite to said first direction.

2. The exercise apparatus of claim 1 further comprising means for varying the magnitude of the force applied in opposition to the rotatable movement of said upper and lower aerobic exercising means.

3. The exercise apparatus of claim 2 wherein said upper and lower body exercising means each comprise a pair of cranks adapted to transmit rotational movement to said common rotable shaft in a first direction.

4. The exercise apparatus of claim 2 wherein said opposition force varying means comprises a pressure regulator adapted to govern the hydraulic pressure applied to said hydraulic pump.

5. The exercise apparatus of claim 4 wherein said upper body pair of cranks is mounted to said frame by means to permit said pair of cranks to be maintained in a stowed position.

6. The exercise apparatus of claim 4 wherein each of said upper and lower body pair of cranks is connected to said common rotable shaft by a linkage.

7. The exercise apparatus of claim 4 further comprising a handlebar assembly connected to said frame.

8. The exercise apparatus of claim 7 further comprising a seat assembly connected to said frame.

9. An exercise apparatus comprising:
   a frame adapted to support a user thereon;
   means adapted to be manipulated by said user to provide an aerobic exercise movement;
   means for providing a load in opposition to said aerobic exercise movement;
   means for storing a pre-determined heart rate value;
   means for alerting said user to the presence of a sensed heart rate value in excess of said pre-determined heart rate value,
   means for reducing the magnitude of the load applied in opposition to said aerobic exercise movement to a predetermined level in response to the presence of a sensed heart rate value in excess of said pre-determined heart rate value; and
   means for discontinuing the load applied in opposition to said aerobic exercise movement in response to the presence of said sensed heart rate value in excess of said pre-determined heart rate value existing for a specific time period.

10. The exercise apparatus of claim 1 further comprising means for increasing the magnitude of said load applied in opposition to said aerobic exercise movement back to its initial magnitude in response to said sensed heart rate value decreasing to a value below said pre-determined value within said specific time period.

11. The exercise apparatus of claim 10 wherein said alerting means comprises an audible alarm.

12. The exercise apparatus of claim 10 further comprising means for displaying said sensed heart rate value to said user.

13. The exercise apparatus of claim 10 further comprising a timer to display a desired exercise period to said user.

14. An exercise apparatus comprising:

a frame adapted to support a user thereon;
manually actuable means carried by said frame for providing an aerobic exercise movement;
means for providing a force to said manually actuable means in opposition to said aerobic exercise movement; said means having three operational modes with said first mode imparting a larger magnitude opposition force than said second mode and said second mode imparting a larger magnitude opposition force than said third mode;
means for sensing the heart rate of said user;
means responsive to said sensing means for actuating said opposition force means into said first operational mode when sensed heart rate is below a pre-determined value and into said second operational mode for a prescribed period of time when the sensed heart rate is above said predetermined value; and
means responsive to said sensing means for actuating said opposition force means into said third operational mode which discontinues the opposition force applied to said manually actuable means when the sensed heart rate value is in excess of said pre-determined value for a specific period of time.

* * * * *